US008598557B2

(12) United States Patent
Cochran et al.

(10) Patent No.: US 8,598,557 B2
(45) Date of Patent: Dec. 3, 2013

(54) METHOD AND APPARATUS FOR PROVIDING PATTERNED ILLUMINATION FIELDS FOR MACHINE VISION SYSTEMS

(75) Inventors: Don W. Cochran, Novelty, OH (US); Steven D. Cech, Aurora, OH (US); Thomas H. Palombo, Cuyahoga Falls, OH (US); Michael L. Yoder, Wadsworth, OH (US); Jesse C. Booher, Solon, OH (US); Terry L. Graves, Wadsworth, OH (US)

(73) Assignee: Pressco Technology Inc., Cleveland, OH (US)

( * ) Notice: Subject to any disclaimer, the term of this patent is extended or adjusted under 35 U.S.C. 154(b) by 0 days.

(21) Appl. No.: 10/519,180

(22) PCT Filed: Jun. 20, 2003

(86) PCT No.: PCT/US03/19580
§ 371 (c)(1),
(2), (4) Date: Aug. 18, 2005

(87) PCT Pub. No.: WO04/001285
PCT Pub. Date: Dec. 31, 2003

(65) Prior Publication Data
US 2006/0091333 A1    May 4, 2006

Related U.S. Application Data

(60) Provisional application No. 60/390,839, filed on Jun. 21, 2002.

(51) Int. Cl.
*G01N 21/86* (2006.01)
*G01N 21/00* (2006.01)
(52) U.S. Cl.
USPC .................................. 250/559.34; 356/237.2

(58) Field of Classification Search
USPC ................ 250/559.16, 559.45, 223 R, 223 B; 356/394, 237.1–237.5, 603, 604, 612
See application file for complete search history.

(56) References Cited

U.S. PATENT DOCUMENTS 4,882,498 A * 11/1989 Cochran et al. .......... 250/559.04
4,893,223 A   1/1990 Arnold
(Continued)

FOREIGN PATENT DOCUMENTS

JP    08254417 A  * 10/1996

OTHER PUBLICATIONS

International Search Report corresponding to International Application No. PCT/US03/19580.

(Continued)

*Primary Examiner* — Thanh Luu
(74) *Attorney, Agent, or Firm* — Fay Sharpe LLP (57) ABSTRACT

This application relates to an apparatus and method for providing patterned illumination fields for use within process control and article inspection applications. More specifically, it pertains to the use of patterned illuminators to enable visual surface inspection of polished objects such as ball bearings. The use of patterned illuminators properly disposed in relation to a polished part under inspection allows small surface imperfections such as scratches and pits to become visible against the normal surface background. The use of carefully engineered illuminators facilitates advantageous defect-site scattering from generally dark field sources. The patterned nature of the illuminators defined by this invention allows the complete surface of three-dimensional parts to be effectively highlighted using dark field illumination fields.

17 Claims, 6 Drawing Sheets

(56) References Cited

U.S. PATENT DOCUMENTS

| | | | |
|---|---|---|---|
| 5,004,909 A * | 4/1991 | Fukuchi | 250/223 B |
| 5,072,127 A * | 12/1991 | Cochran et al. | 250/559.39 |
| 5,684,530 A * | 11/1997 | White | 348/131 |
| 5,691,811 A * | 11/1997 | Kihira | 356/239.1 |
| 5,909,285 A | 6/1999 | Beaty et al. | |
| 5,943,125 A | 8/1999 | King et al. | |
| 6,118,524 A | 9/2000 | King et al. | |
| 6,191,850 B1 * | 2/2001 | Chiang | 356/237.4 |
| 6,207,946 B1 * | 3/2001 | Jusoh et al. | 250/208.1 |
| 6,238,060 B1 | 5/2001 | Bourn et al. | |
| 6,256,091 B1 | 7/2001 | Kobayashi | |
| 6,273,338 B1 * | 8/2001 | White | 235/462.42 |
| 6,341,878 B1 | 1/2002 | Chiang | |
| 6,359,694 B1 | 3/2002 | Stredele et al. | |
| 6,542,236 B1 * | 4/2003 | Kim | 356/394 |
| 6,554,452 B1 * | 4/2003 | Bourn et al. | 362/247 |
| 6,788,411 B1 * | 9/2004 | Lebens | 356/394 |

OTHER PUBLICATIONS

Bachelor, Hill and Hodgson (editors), Automated Visual Inspection, Chapters 4-7, 17 and 19, IFS (Publications) Ltd. (1985).

* cited by examiner

METHOD AND APPARATUS FOR PROVIDING PATTERNED ILLUMINATION FIELDS FOR MACHINE VISION SYSTEMS

This application claims priority to the prior provisional patent application entitled "Patterned Illumination Method and Apparatus for Machine Vision Systems" bearing U.S. Ser. No. 60/390,839, filed Jun. 21, 2002.

BACKGROUND OF THE INVENTION

This application relates to an apparatus and method for providing patterned illumination fields for use within process control and article inspection applications. More specifically, it pertains to the use of patterned illuminators to enable visual surface inspection of polished objects such as ball bearings. While the invention is particularly directed to the art of high-speed automated process control and article inspection applications, and will be thus described with particular reference thereto, it will be appreciated that the invention may have usefulness in other fields and applications. For example, the invention may be used as an illumination source for manual or operator-initiated inspection of parts.

By way of background, the use of engineered lighting systems within automated inspection systems is well known in the art. For example, U.S. Pat. No. 4,882,498 entitled "Pulsed-Array Video Inspection Lighting System" describes a method and apparatus related to engineered lighting system for machine vision applications. Amongst other things this invention introduces the concepts of spatially distributing and high-current pulsing solid-state lighting elements within the engineered illumination system. Both of these innovations worked to allow autonomous machine vision to be advantageously applied to an expanding class of application areas. Similarly, U.S. Pat. No. 6,238,060 entitled "Machine Vision Ring-Reflector Illumination System and Method" describes an innovation related to the implementation of a ringlight-based illumination system. One embodiment of this referenced patent is an illumination system capable of generating configurable dark field illumination. There is a volume of prior art descriptions which indicates the appropriateness and usefulness of dark field illumination to highlight surface anomalies (such as scratches and pits) occurring on generally flat polished surfaces. While introducing improvements in the areas of ease of deployment and dark field configurability, the referenced invention is limited in generally the same fashion as all prior art ringlight implementations in regards to its ability to provide complete and uniform illumination fields for the case of contoured, 3-dimensional, specular surfaces. On these classes of parts, the directional lighting associated with ringlight illumination causes uneven returns from the part under inspection. In addition to getting scatter-induced reflections at defect locations such as scratches and pits (which are preferred), intense image artifacts are also generated at all locations wherein the local surface orientation (due to normal part contours) allow light emitted by the ringlight source to be specularly-reflected into the receiver aperture of an associated inspection system. As these image artifacts or hot-spots are typically intense enough so as to drive any receiving entity into high scale saturation, inspection (automated or otherwise) is not generally possible in these areas. In addition, due to general shadowing effects caused by the 3-dimensional nature of the part under inspection, it is possible for areas of the part to receive little to no incident illumination if ringlight or other dark field illumination technique is exclusively used to image these classes of parts.

Many of the objects typically inspected using automated machine vision systems happen to be specular and 3-dimensional in nature. Included in this list are metal cans and closures, ball bearings, electrical contacts, and populated electrical assemblies. To adequately inspect these and other complex parts, hundreds of additional prior art improvements to the illumination portions of these inspection systems have been devised and implemented. To address the specific inspection needs associated with highly specular, 3-dimensional parts, various forms of an illumination system typically described as a continuous, diffuse illuminator have been designed, constructed, and applied within inspection systems. They are well known in the art. Such a continuous diffuse system was described in the 1985 textbook, *Automated Visual Inspection*, by Batchelor, Hill, and Hodgson. These lighting systems differ from directional ring light sources in that they are designed to generate lighting fields that illuminate parts under inspection from essentially all directions. These illuminators often take the geometric form of a hemisphere surrounding the part under inspection. Constructed in this manner, continuous, diffuse lighting systems allow uniform gray scale images of highly specular, 3-dimensional parts to be acquired. Images that are generally uniform in gray scale intensity advantageously enable automated, high-speed analysis. When illuminated in this fashion, specular, 3-dimensional parts can be adequately inspected for a number of classes of defects including absorptive-type defects (such as contamination) as well as gross part deformations.

While it is sometimes possible to detect surface scratches or pits using continuous diffuse lighting systems, the performance of these systems on these classes of defects is not optimal. The angularly-uniform and complete nature of the impinging light stimulus creates a condition wherein scatter effects caused by surface scratches and the like are effectively blanketed over and masked by natural specular reflections occurring on the surrounding non-defective surface. To best highlight these types of defects on highly specular parts, it is still best to use directional lighting.

As an illustration of one specific example of a continuous, diffuse lighting system, U.S. Pat. No. 6,341,878 entitled "Method and Apparatus for Providing Uniform Diffuse Illumination to a Surface" describes an improvement in the state of the art of uniform diffuse illumination which places the emitting light source below the part under inspection. In doing so, the ability of the lighting system to generate low angle illumination is improved. This invention also references a hemispherical diffuser located above the part under inspection and the deployment of crossed linear polarizers (one over the emitting light elements and one at the receiver aperture).

The present invention overcomes difficulties noted above and others. It also provides distinct advantages over heretofore known systems.

SUMMARY OF THE INVENTION

The present invention is directed to an apparatus and method of providing patterned lighting fields to support the visual inspection of highly specular, 3-dimensional parts. The disclosed illuminator consists of a source of patterned, diffuse light that is situated largely above an object being inspected. In a preferred embodiment, this upper light source is implemented as a hemispherical reflector or diffuser wherein the patterned zones of illumination are laid out in annular rings about a central view port. Located below the part being inspected is an additional diffuse, patterned light source. This light source is used to generate patterned low angle illumination that is required for some part geometries. In a preferred embodiment, the lower illuminator is implemented as a 2-dimensional panel source wherein the patterned zones are laid out in annular zones about a central axis.

In one aspect of the present invention, a directional illuminator is provided that is constructed in a fashion wherein the image hot-spot artifacts created by specular reflections off of areas of non-defective part surfaces are of the variety which enable autonomous processing and detection operations to occur.

In another aspect of the present invention, an illuminator is provided that is constructed to provide advantageous directional or dark field illumination over controlled areas across the entire surface of a specular, 3-dimentional part.

In another aspect of the invention, a patterned illuminator is provided which produces a controlled hot-spot pattern within the acquired image field that both allows existing defect detection algorithms to execute while, in addition, provides directional or dark field illumination to selected and controlled areas across the entire part surface. This combination of illuminator attributes enables the high-performance, automated inspection of highly specular, 3-dimensional parts for the presence of critical surface defects such scratches or pits.

In another aspect of the invention, the system comprises a patterned illuminator configured to provide spatially-adjacent regions of uniform, diffuse lighting and lighting voids to produce engineered illumination fields, a receiver aperture positioned to receive light generated by the patterned illuminator which has scattered or reflected off a part under inspection and a transport mechanism used to automatically convey and position parts under inspection within the engineered illumination fields generated by the patterned illuminator.

In another aspect of the invention, the patterned illuminator is implemented as a series of annular regions alternating between diffuse, uniform illumination and lighting voids.

In another aspect of the invention, the patterned illuminator is implemented using translucent diffusers having a light blocking annular pattern superimposed on their surfaces, said diffusers being backlit by lighting elements.

In another aspect of the invention, the patterned illuminator is implemented using diffuse reflecting surfaces having a light absorbing annular pattern superimposed on their surfaces, said diffusers being front lit by lighting elements.

In another aspect of the invention, the patterned illuminator is implemented out of a series of discrete ring lights of various dimensions positioned to create the preferred alternating pattern of illumination.

In another aspect of the invention, lighting elements of the patterned illuminator are LEDs.

In another aspect of the invention, the LEDs are operated in a pulsed-mode to support stop action imaging of the objects under inspection.

In another aspect of the invention, the receiver aperture contains a camera capable of generating a two-dimensional image in electronic format of the object under test as it appears illuminated using the patterned illuminator.

In another aspect of the invention, the receiver aperture additionally contains a processor means to autonomously process the electronic image information into a status summary report indicative of the quality or status of the part under inspection.

In another aspect of the invention, the method comprises positioning a part under inspection at a selected location relative to a patterned illuminator wherein illumination fields of the illuminator are selectively activated in an alternating on/off manner to produce an engineered illumination pattern, illuminating the part under inspection using the engineered illumination pattern produced by the patterned illuminator and analyzing light generated by the patterned illuminator that has subsequently reflected or scattered off the part under inspection for the purpose of deducing quality status information related to the part.

In another aspect of the invention, the method comprises positioning the part under inspection at a second location wherein the illumination fields of the illuminator are selectively activated in an alternating on/off manner to produce an engineered illumination pattern such that an inverse engineered illumination pattern is enacted upon the surfaces of the part, illuminating the part under inspection using the inverse engineered illumination pattern produced by the patterned illuminator and analyzing the light generated by the patterned illuminator that has subsequently reflected or scattered off the part under inspection for the purpose of deducing quality status information related to the part.

An advantage of the present invention is that it provides directional lighting across the full surface of highly specular, 3-dimensional parts.

Another advantage of the present invention is that it produces controlled hot-spot image artifacts that allow high-speed automated inspections to take place.

Yet another advantage of the present invention is that it allows highly specular, 3-dimensional parts to be inspected for the presence of critical surface flaws such as scratches and pits.

Further scope of the applicability of the present invention will become apparent from the detailed descriptions provided below. It should be understood, however, that the detailed descriptions and specific examples, while indicating preferred embodiments of the invention, are given by way of illustration only, since various changes and modifications within the spirit and scope of the invention will become apparent to those skilled in the art.

DETAILED DESCRIPTION OF THE DRAWINGS

The present invention exists in the construction, arrangement, and combination of the various parts of the device, and steps of the method, whereby the objects contemplated are attained as hereinafter more fully set forth and illustrated in the accompanying drawings which.

DETAILED DESCRIPTION OF THE INVENTION

Figure 1:
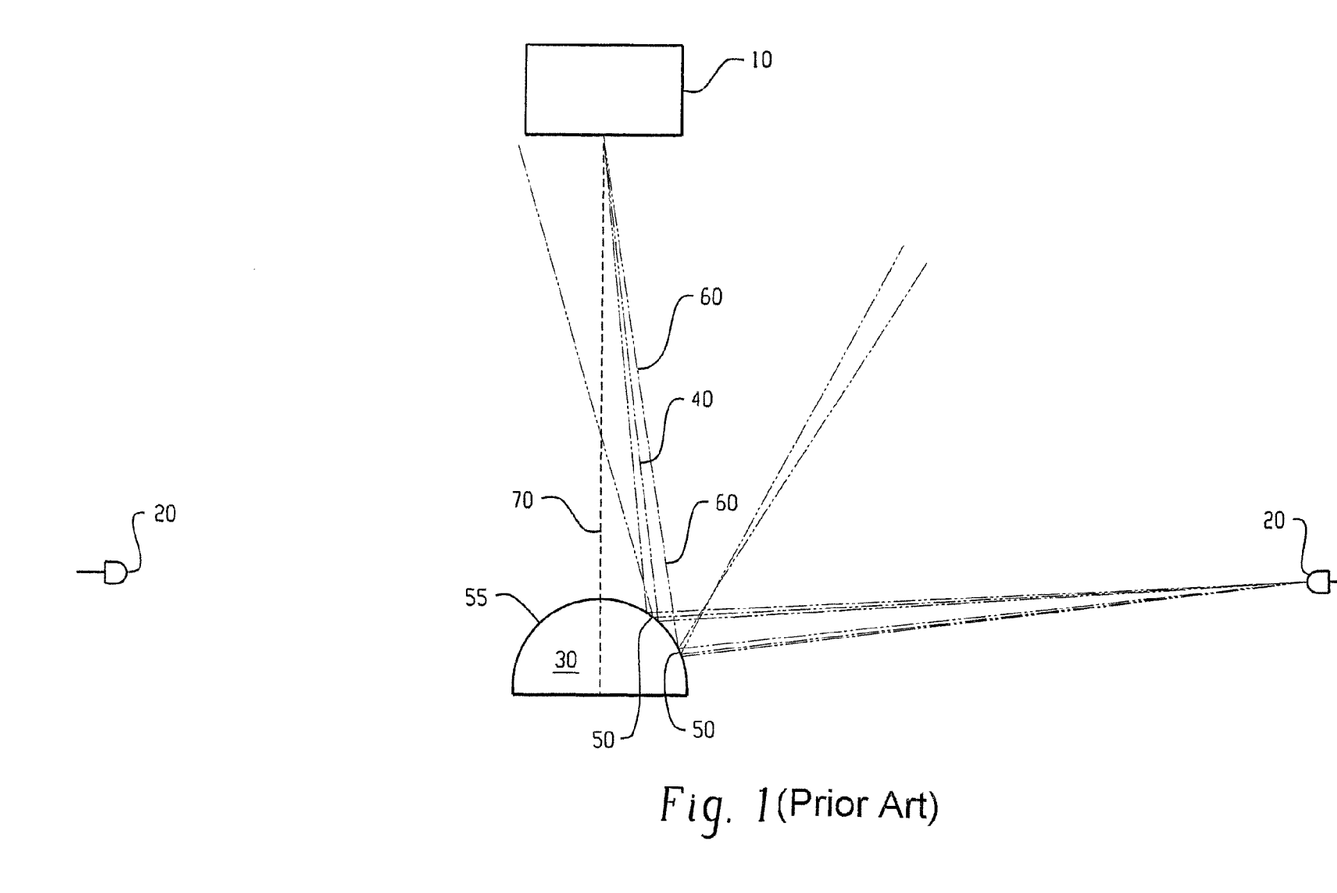
FIG. 1 is a cross-sectional schematic diagram of a prior art ringlight source capable of generating dark field illumination over only a portion of a hemispherically-shaped part.

Referring now to the drawings wherein the showings are for the purposes of illustrating preferred embodiments of the invention only and not for purposes of limiting the same, FIG. 1 provides a cross-sectional schematic view of a prior art ringlight illuminator. As shown, the part under inspection 30 is illustrated as a domed object approaching the general shape of a hemisphere. Note that this choice of part shape is done for the purposes of illustration and should not be interpreted so as to limit in any manner the applicability of this invention to other areas of inspection.

In this prior art implementation, light-emitting diodes (LEDs) 20 are deployed in an annular fashion and are used to generate a line source of generally narrow spatial extent that diverges from its emission point and is directed onto the surface 55 of a centrally located part under inspection 30. In this Figure, a single optical ray 40, emitted by the LED source 20, is ejected at an angle wherein a direct specular reflection off of the normal surface contour results in the ray being directly received at a receiver aperture 10. A bright image artifact or hot-spot will be formed in this position in an annular pattern of constant radius about the part/receiver aperture axis 70. The perceived width of this specular image artifact will be dependent on the spatial extent of the LED source 20 and the physical extent of the receiver aperture 10. Also indicated on this Figure are tow areas on the surface 55 of the part of local surface perturbation or defect 50. In these areas, due to the presence of scratches, pits, dents, etc., the part surface 55 deviates from its normal figure. These deviations, depending on their depth and orientation, can scatter incident photons that would not otherwise be detected into the active region of the receiver aperture 10.

This simplified presentation outlines the process wherein directional or dark field lighting can be enacted to stimulate the detection of scratches or the like on the surface of specular surfaces. The two rays identified as 60 are rays that have undergone this type of advantageous scattering action.

Figure 2:
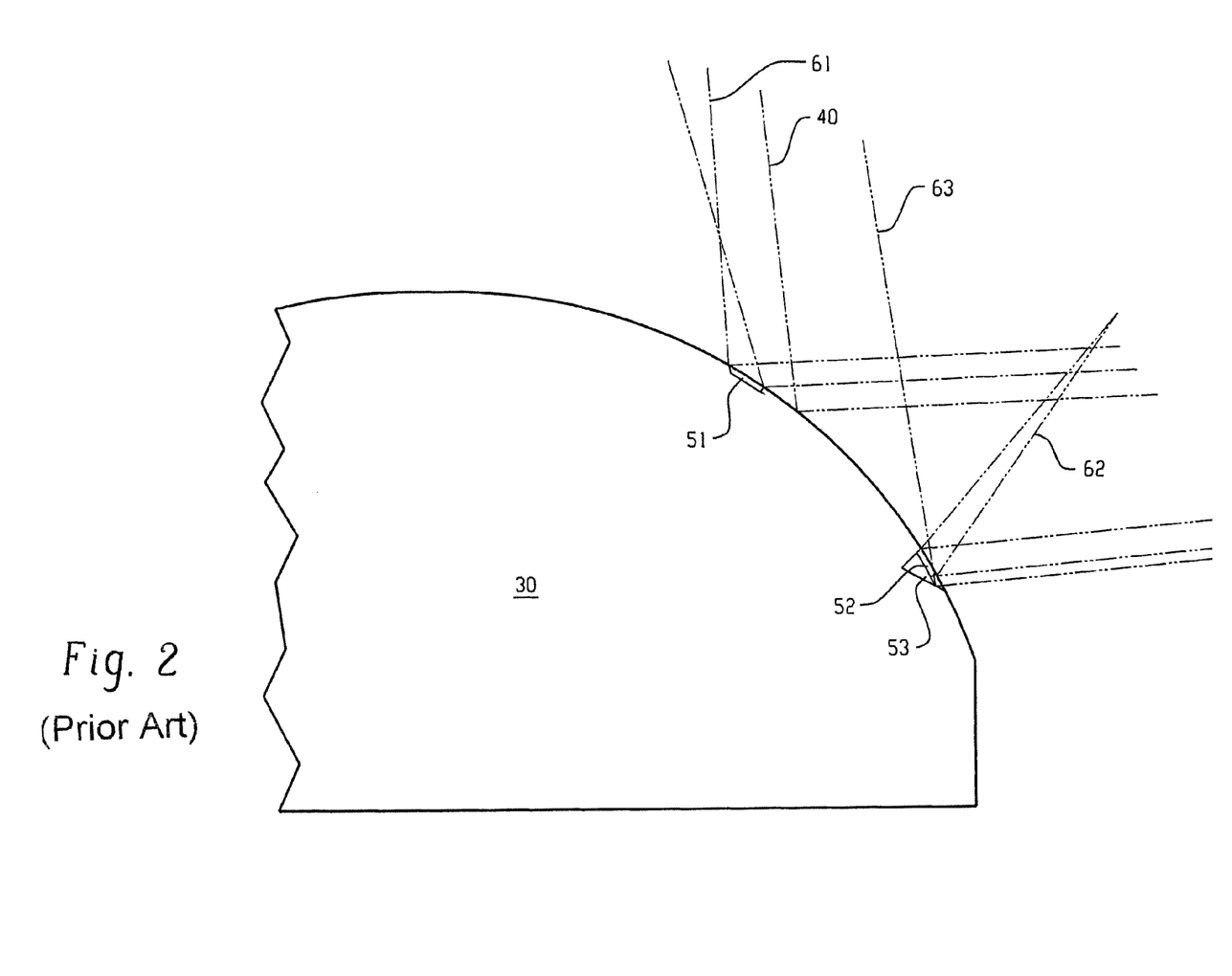
FIG. 2 is a close-up schematic representation of the interaction of light rays at the surface of specular, 3-dimensional surface.

FIG. 2 depicts a close-up schematic view of the interaction of incident dark field illumination with a part under inspection 30. In FIG. 2, the specular ray 40 is identified as it has been discussed above. Surface defects 51, 52 and 53 are indicated on the part surface 55. As it is indicated in this Figure, the relatively shallow indentation associated with defect 51 allows dark field illumination as described in FIG. 1 to reflect in a direction which would allow entrance into the receiver aperture 10. Ray 61 represents the scatter-induced reflection off of the indented surface of defect 51. A surface perturbation drawn to the same general depth as defect 51 but placed in a different location on the part 30 (indicated as defect 52) results in a completely different degree of detectability using this same ringlight source. Ray 62 represents the scatter-induced ray generated by defect 52. Ray 62 does not reach the receiver aperture 10 as defined in FIG. 1 and, therefore, would go undetected. By drawing the depth of the surface defect down as is indicated by defect 53, it is possible to generate a ray 63 that is scattered by a simple ringlight source in a direction advantageous to its detection.

What can be concluded from this simplified analysis of the physics of reflection at the surface of a specular surface is that a defect's degree of perturbation as well as its proximity to the location of the dark field specular artifact both have an impact on its detectability. Defect 51 is relatively close to the specular ray 40 and, therefore, it does not take much surface perturbation at this location to enact advantageous scattering. In contrast, the location of defects 52 and 53 are relatively removed from the specular ray 40 and, consequently, only the gross defect 53 is detectable.

Figure 3:
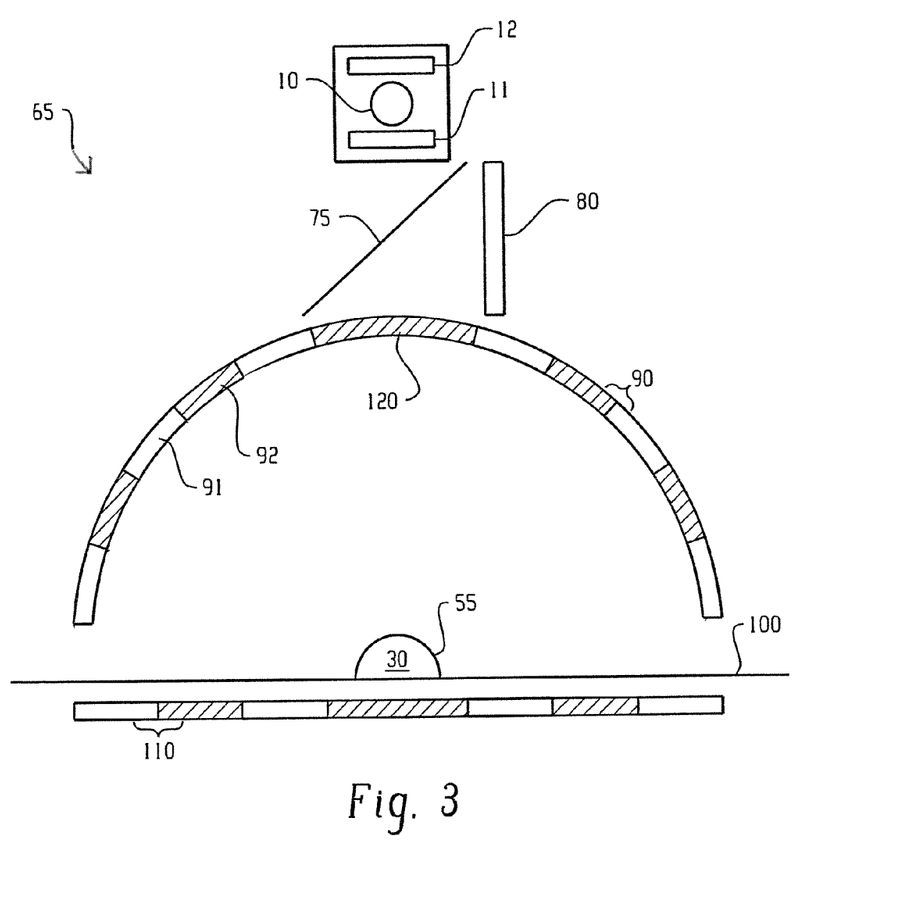
FIG. 3 is a block diagram illustrating an illuminator according to the present invention.

With this as background, FIG. 3 is now presented and represents the preferred embodiment of the present invention. In the preferred embodiment, the part under inspection 30 is fixtured within the illuminator 65 via a support/transport mechanism 100. Located above the part under inspection 30 is a patterned diffuse light source 90, preferably constructed in the form of a hemisphere. In the preferred embodiment, the support transport mechanism 100 is constructed in a fashion that allows illumination to be incident on the part 30 from below. In this manner, an additional patterned diffuse light source 110 can be deployed to provide advantageous illumination from below the part 30. The patterned light sources 90 and 110 are preferably constructed to provide spatially alternating areas of intense uniform light 91 and dark areas or lighting voids 92. This alternating pattern of intense light 91 and lighting voids 92 creates a pattern, within the reflected image field, of structured specular regions adjacent to regions of advantageous dark field illumination as it has been described in reference to FIGS. 1 and 2. In these dark field regions, the detection of surface defects such as scratches or pits will be optimized. Within the adjacent specular regions, defect detection will still be as good or better than that attainable using continuous diffuse lighting techniques. If preferred dark field illumination is required over all surface areas of the part, a second illuminator configured with the alternate illumination pattern can be deployed in sequence with the original illuminator 65. One skilled in the art of machine vision illumination will understand that by making adjustments to the spacing (size of dark versus light areas) that signal-to-noise ratio can be further optimized for various types of surface defects. One skilled in the art will also understand the patterned illuminator (e.g. patterned light sources 90 and 110) may well be comprised of light emitting diodes (LEDs). These LEDs may be operated in a variety of different modes including a pulsed mode to support stop action imaging of the objects under inspection.

In the preferred embodiment, the intense light 91 and lighting void 92 regions are defined as alternating annular regions alternating between diffuse, uniform illumination and lighting voids. A patterned illuminator constructed using such concentric regions results in a part image containing alternating dark and bright concentric regions. Many parts that are inspected using automated machine vision systems are generally round in nature. Inspection algorithms that are designed to operate within specific annular regions of the imaged part are well known in the art. For this reason, a patterned illuminator that creates annular zones of inspection is preferred. However, the spirit of the inventions includes the implementation-of a patterned illuminator of arbitrary pattern.

Additionally, within the scope of the present invention, the alternating illumination pattern can, in an alternate construction, be fabricated as regions of alternating spectral properties. With the deployment of proper spectral filtering within the receiving aperture 10 of the illuminator 65, advantageous dark field illumination can still be enacted over the part surface 55. For example, by utilizing two different wavelengths of light (through use of LEDs of differing wavelengths), it is possible to use two different cameras—each filtered to only see its respective wavelengths and thus have continuous coverage by selected treatment of the respective camera image information.

Integrated as part of the hemispherical upper light source 90 is a view port 120. The view port 120 allows a receiving aperture 10 to be positioned to receive reflected or scattered light coming off the part under inspection 30. It should be understood that the receiving aperture 10 typically contains a camera 11 (only representatively shown as a part of receiving aperture 10) that is preferably operative to generate a two-dimensional image of the object 30. The image is preferably in electronic format to facilitate ease of processing and is preferably obtained upon appropriate illumination of the object. It should be understood that the receiving aperture 10 also preferably includes a processor 12 (only representatively shown as a part of receiving aperture 10), or processing means, to process the image obtained by the camera of receiving aperture 10. The processor may then produce a status summary report indicative of the quality or status of the object 30, or the part under inspection. As is well known, the quality or status report may result in or take the form of a reject signal that is provided to a reject mechanism (not shown) in the system to remove the object from the support/transport mechanism 100. In some embodiments, the reject mechanism takes the form of an air blowing mechanism that is operated under the control of the processor to blow objects from the mechanism 100. Alternatively, the summary report may simply be provided to a user or the processor for consideration in further processing decisions.

Provision is also made within the preferred embodiment for the placement of a beamsplitter component 75 between the hemispherical light source 90 and receiving aperture 10. The beamsplitter 75 is used to re-direct light generated by center light source 80 into the location of the view port 120. This completes the continuous nature of the incident lighting fields.

The patterned illuminators 90 and 110 are preferably fabricated as translucent diffusers backlit by lighting elements. The spatial illumination pattern key to the present illumination is preferentially created by placing a masking element or a light blocking annular element on the surface or, alternatively, within the volume of alternating and adjacent regions of the diffuser. In the case of the upper hemispherical light source, an alternate means of creating the patterned light source is to use a patterned reflector dome having a light absorbing annular pattern designed to reflect (in alternating high-reflectivity/low-reflectivity annular regions) incident light emitted by the lower backlight source 110. Implemented in this fashion, a reflector dome as defined appears, to the part under inspection 30, as if it were a primary source of the required patterned illumination. Again, one skilled in the art will also understand the backlight source 110 may well be comprised of light emitting diodes (LEDs). These LEDs may be operated in a variety of different modes including a pulsed mode to support stop action imaging of the objects under inspection.

Figure 6:
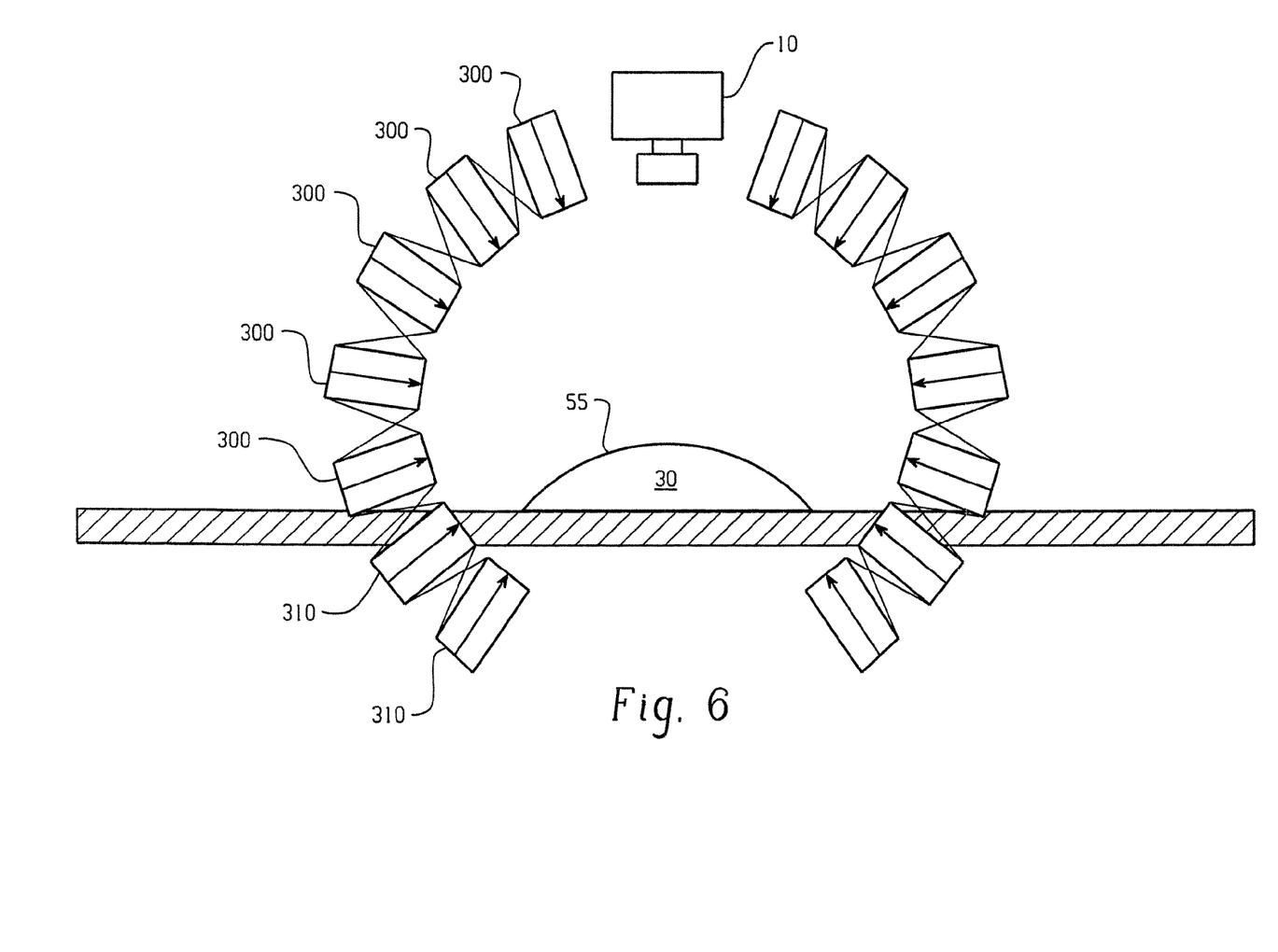
FIG. 6 is an illustration of an alternative embodiment of the present invention.

An alternative embodiment would be as shown in FIG. 6 wherein a series of ring lights 300, and ring lights 310, would be configured such that there is a dark space (no light produced) between each of the ring lights. They would form a hemisphere which would produce light in alternate annular rings. Also shown are the aperture 10 and object 30 having a surface 55. As with other embodiments contemplated herein, one skilled in the art will also understand the ring lights 300 and 310 may well be comprised of light emitting diodes (LEDs). These LEDs may be operated in a variety of different modes including a pulsed mode to support stop action imaging of the objects under inspection.

Figure 4:
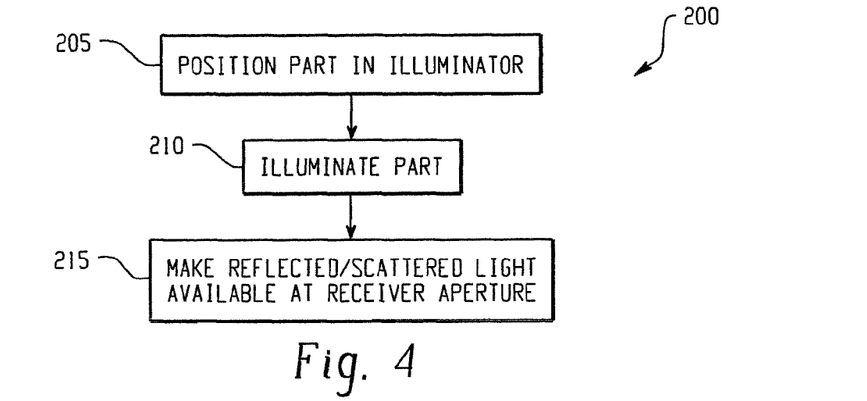
FIG. 4 is a flow chart illustrating the preferred lighting method according to the present invention.

Referring now to FIG. 4, one preferred illumination method 200 reflecting the basic steps of operation is shown. Initially, the part under inspection 30 is positioned in a preferred location within the illuminator 65 (step 205). Light energy from the illuminator 65 is directed onto the surface of the part 55 (step 210). In this regard, illumination fields of the illuminator are selectively activated in an alternating on/off manner to produce an engineered illumination pattern. Finally, light reflected or scattered off the part (such reflection or scattering containing information related to the part's quality) is made available for detection at the receiver aperture 10 (step 215). Notably, the light generated by the patterned illuminator that reflected or scattered off the part under inspection is captured by, for example, the camera and analyzed by, for example, the processor for the purpose of deducing quality status information related to the part. As indicated above, a summary report may then be produced.

Figure 5:
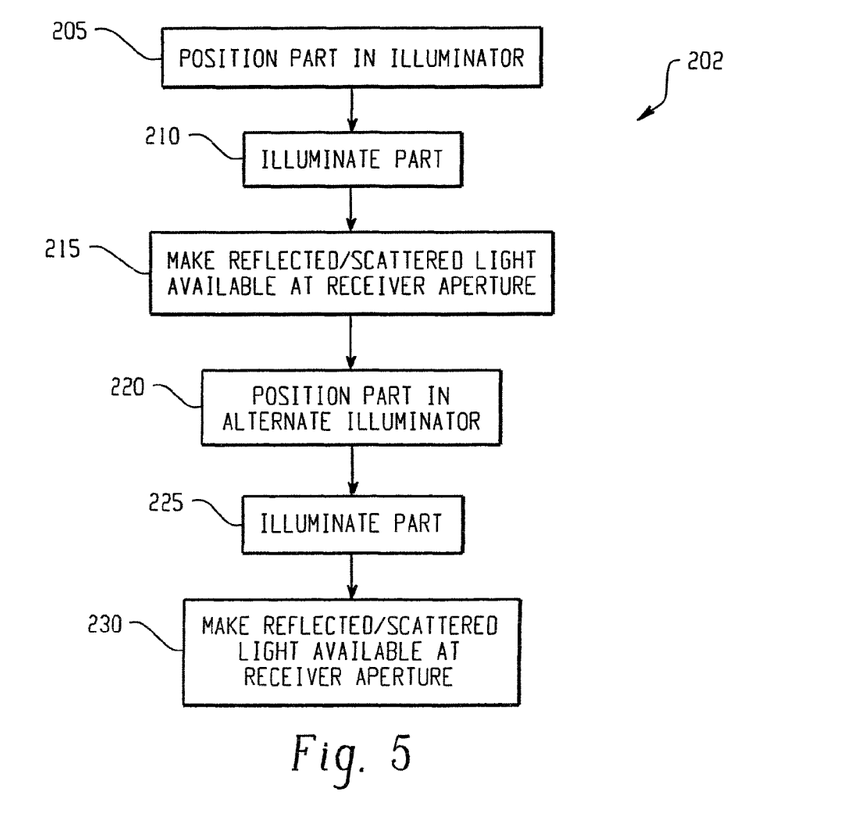
FIG. 5 is a flow chart illustrating an alternate lighting method according to the present invention.
Figure 7:
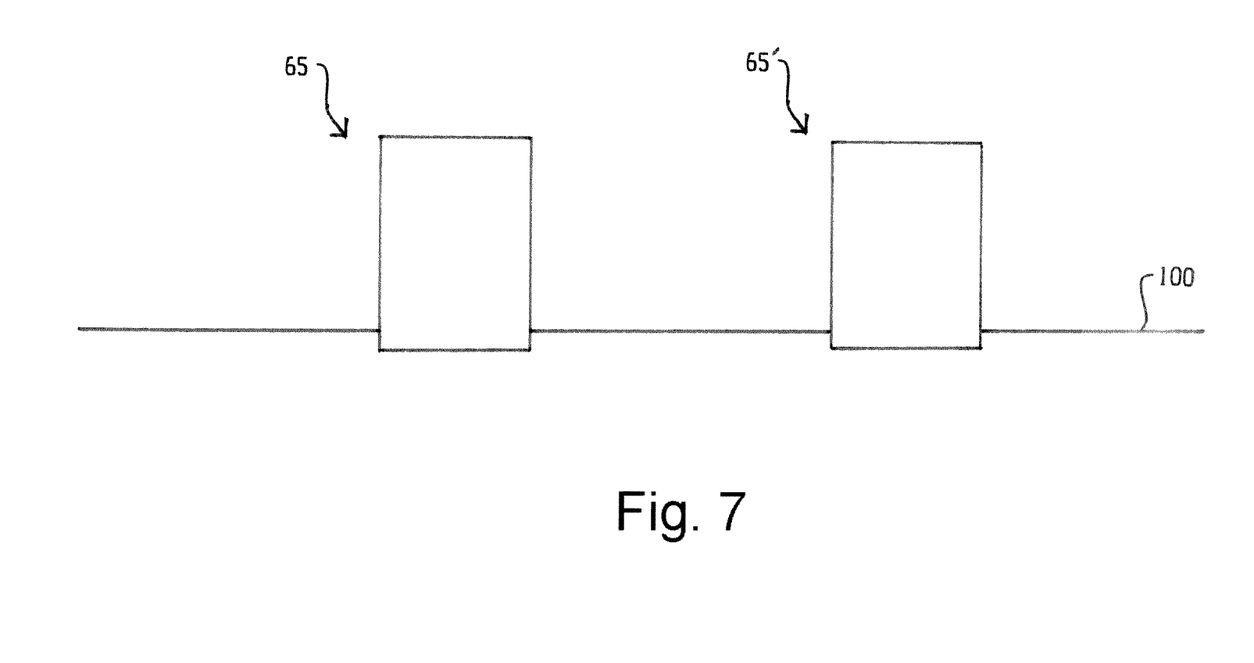
FIG. 7 is an illustration of an alternative embodiment of the present invention.

Alternately, FIG. 5 describes an extension of the basic method 200 wherein a second illuminator (65', FIG. 7) is used in sequential fashion with the first illuminator 65 (also shown in FIG. 7) method (202). In method 202, the second or alternate illuminator 65' is configured having a complementary intense light 91/lighting void 92 pattern as compared to the original 5 patterned illuminator 65. As defined, the additional steps outlined as 220, 225, and 230, performed after steps 205, 210, and 215, effect complete coverage of the parts surface 50 using preferential dark field illumination.

In this regard, after steps 205, 210 and 215 are competed, the part under inspection is positioned at a second location wherein the illumination fields of an illuminator 65' are selectively activated in an alternating on/off manner to produce an engineered illumination pattern such that an inverse engineered illumination pattern is enacted upon the surfaces of the part (step 220). This illuminator 65' is preferably a separate, alternate illuminator. The part under inspection is then illuminated using the inverse engineered illumination pattern produced by the alternate, patterned 15 illuminator (step 225). Last, the light generated by the patterned illuminator that has subsequently reflected or scattered off the part under inspection is made available for the purpose of deducing quality status information related to the part (step 230). As with the method 200, the light generated by the patterned illuminator that reflected or scattered off the part under inspection is captured by, for example, the camera. The processor then analyzes the information that is captured for the purpose of deducing quality status information related to the part. As indicated above, a summary report may then be produced.

The above description merely provides a disclosure of particular embodiments of the invention and is not intended for the purposes of limiting the same thereto. As such, the invention is not limited to only the above-described embodiments. Rather, it is recognized that one skilled in the art could conceive alternative embodiments that fall within the scope of the invention.

What is claimed is:

1. A system for providing patterned illumination fields within an automated visual inspection system, the system comprising:
   a patterned illuminator comprising light emitting diodes (LEDs) and at least one masking or blocking element to provide lighting voids and configured to provide spatially-adjacent concentric annular regions of uniform, diffuse lighting and the lighting voids to produce engineered illumination fields on a highly specular three-dimensional part under inspection;
   a receiver aperture positioned to receive light of a reflected image field including dark field regions corresponding to the lighting voids generated by the patterned illuminator, wherein the dark field regions allow for illumination and detection of a specular artifact on the part under inspection; and
   a transport mechanism used to automatically convey and position highly specular, three-dimensional parts within the engineered illumination fields generated by the patterned illuminator.

2. The system as set forth in claim 1 wherein the patterned illuminator comprises a series of the annular regions alternating between diffuse, uniform illumination and lighting voids.

3. The system as set forth in claim 2 wherein the patterned illuminator comprises translucent diffusers having a light blocking annular pattern superimposed on surfaces thereof.

4. The system as set forth in claim 2 wherein the patterned illuminator comprises diffuse reflecting surfaces having a light absorbing annular pattern superimposed on surfaces thereof.

5. The system as set forth in claim 3 wherein the LEDs are operated in a pulsed-mode to support stop action imaging of objects under inspection.

6. The system as set forth in claim 4 wherein the LEDS are operated in a pulsed-mode to support stop action imaging of objects under inspection.

7. The system as set forth in claim 1 wherein the LEDs are operated in a pulsed mode to support stop action imaging of objects under inspection.

8. The system as set forth in claim 1 wherein the receiver aperture contains a camera capable of generating a two-dimensional image in electronic format of the part under inspection as it appears illuminated using the patterned illuminator.

9. The system as set forth in claim 8 wherein the receiver aperture additionally contains a processor means to autonomously process electronic image information into a status summary report indicative of the quality or status of the part under inspection.

10. A method of illuminating a part under inspection within an automated visual inspection system, the method comprising steps of:
positioning a highly specular, three-dimensional part under inspection using a transport mechanism at a selected location relative to a patterned illuminator comprising light emitting diodes (LEDs) and at least one masking or blocking element to provide lighting voids wherein illumination fields of the illuminator are selectively activated in an alternating on/off manner to produce an engineered illumination pattern;
illuminating the part under inspection using the engineered illumination pattern produced by the patterned illuminator; and
analyzing light of a reflected image field including dark field regions corresponding to the lighting voids generated by the patterned illuminator, wherein the dark field regions allow for illumination and detection of a specular artifact on the part under inspection for the purpose of deducing quality status information related to the part.

11. The method as set forth in claim 10 comprising additional steps of:
positioning the part under inspection using the transport mechanism at a second location wherein the illumination fields of a second illuminator are selectively activated in an alternating on/off manner to produce an engineered illumination pattern such that an inverse engineered illumination pattern is enacted upon the surfaces of the part;
illuminating the part under inspection using the inverse engineered illumination pattern produced by the second illuminator; and
analyzing the light generated by the second illuminator that has subsequently reflected or scattered off the part under inspection for the purpose of deducing quality status information related to the part.

12. A system for providing patterned illumination fields within an automated visual inspection system, the system comprising:
a patterned illuminator comprising light emitting diodes (LEDs) configured to provide spatially-adjacent concentric annular regions of uniform, diffuse lighting and lighting voids to produce engineered illumination fields on a highly specular, three-dimensional part, wherein the patterned illuminator comprises a series of discrete ring lights of various dimensions positioned to create an alternating concentric annular pattern of illumination;
a receiver aperture positioned to receive light of a reflected image field including dark field regions corresponding to the lighting voids generated by the patterned illuminator, wherein the dark field regions allow for illumination and detection of a specular artifact on the highly specular, three-dimensional part under inspection; and
a transport mechanism used to automatically convey and position highly specular, three-dimensional parts under inspection within the engineered illumination fields generated by the patterned illuminator.

13. A method of illuminating a part under inspection within an automated visual inspection system, the method comprising steps of:
positioning a highly specular, three-dimensional part under inspection using a transport mechanism at a selected location relative to a patterned illuminator comprising light emitting diodes (LEDs) wherein illumination fields of the illuminator are selectively activated in an alternating on/off manner to produce an engineered illumination pattern wherein the patterned illuminator comprises a series of discrete ring lights of various dimensions positioned to create an alternating pattern of illumination;
illuminating the part under inspection using the engineered illumination pattern produced by the patterned illuminator; and
analyzing light of a reflected image field including dark field regions corresponding to lighting voids generated by the patterned illuminator, wherein the dark field regions allow for illumination and detection of a specular artifact on the part under inspection for the purpose of deducing quality status information related to the part.

14. The method as set forth in claim 13 comprising additional steps of:
positioning the part under inspection using the transport mechanism at a second location wherein the illumination fields of a second illuminator are selectively activated in an alternating on/off manner to produce an engineered illumination pattern such that an inverse engineered illumination pattern is enacted upon the surfaces of the part;
illuminating the part under inspection using the inverse engineered illumination pattern produced by the second illuminator; and
analyzing the light generated by the second illuminator that has subsequently reflected or scattered off the part under inspection for the purpose of deducing quality status information related to the part.

15. A method of illuminating a part under inspection within an automated visual inspection system, the method comprising steps of:
positioning a highly specular, three-dimensional part under inspection using a transport mechanism at a selected location relative to a patterned illuminator comprising light emitting diodes (LEDs) and at least one masking or blocking element providing lighting voids and configured to provide spatially-adjacent regions of uniform, diffuse lighting and the lighting voids to produce an engineered illumination pattern on the highly specular three-dimensional part under inspection;

illuminating the part under inspection using the engineered illumination pattern produced by the patterned illuminator; and analyzing light of a reflected image field including dark field regions corresponding to the lighting voids generated by the patterned illuminator, wherein the dark field regions allow for illumination and detection of a specular artifact on the part under inspection for the purpose of deducing quality status information related to the part.

16. A system for providing patterned illumination fields within an automated visual inspection system, the system comprising:

a first and second patterned illuminator, each comprising light emitting diodes (LEDs) and at least one masking or blocking element to provide lighting voids and configured to provide spatially-adjacent concentric annular regions of uniform, diffuse lighting and the lighting voids to produce engineered illumination fields on a highly specular three-dimensional part under inspection, wherein the engineered illumination fields of the first and second patterned illuminators are complementary;

receiver apertures positioned to receive light of a reflected image field including dark field regions corresponding to the lighting voids generated by the patterned illuminators, wherein the dark field regions allow for illumination and detection of a specular artifact on the part under inspection; and a transport mechanism used to automatically convey and position highly specular, three-dimensional parts within the engineered illumination fields generated by the patterned illuminators.

17. A system for providing patterned illumination fields within an automated visual inspection system, the system comprising:

a first and second patterned illuminator, each comprising light emitting diodes (LEDs) configured to provide spatially-adjacent concentric annular regions of uniform, diffuse lighting and lighting voids to produce engineered illumination fields on a highly specular, three-dimensional part, wherein the patterned illuminator comprises a series of discrete ring lights of various dimensions positioned to create an alternating concentric annular pattern of illumination and, wherein the engineered illumination fields of the first and second patterned illuminators are complementary;

receiver apertures positioned to receive light of a reflected image field including dark field regions corresponding to the lighting voids generated by the patterned illuminators, wherein the dark field regions allow for illumination and detection of a specular artifact on the highly specular, three-dimensional part under inspection; and a transport mechanism used to automatically convey and position highly specular, three-dimensional parts under inspection within the engineered illumination fields generated by the patterned illuminators.

* * * * *